United States Patent
Gaemers et al.

(10) Patent No.: US 7,276,626 B2
(45) Date of Patent: Oct. 2, 2007

(54) CARBONYLATION PROCESS USING METAL-TRIDENTATE LIGAND CATALYSTS

(75) Inventors: Sander Gaemers, East Riding of Yorkshire (GB); John Glenn Sunley, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 10/555,417

(22) PCT Filed: May 5, 2004

(86) PCT No.: PCT/GB2004/001943

§ 371 (c)(1),
(2), (4) Date: Nov. 3, 2005

(87) PCT Pub. No.: WO2004/101488

PCT Pub. Date: Nov. 25, 2004

(65) Prior Publication Data

US 2006/0173212 A1  Aug. 3, 2006

(30) Foreign Application Priority Data

May 14, 2003  (GB) .................................. 0311091.3

(51) Int. Cl.
*C07C 51/12*  (2006.01)

(52) U.S. Cl. .................. 562/519; 562/517; 560/232
(58) Field of Classification Search ................. 562/519, 562/517; 560/232
See application file for complete search history.

(56) References Cited

U.S. PATENT DOCUMENTS

| 4,102,920 A | * | 7/1978 | Bartish ........................ 562/519 |
| 4,102,921 A |   | 7/1978 | Bartish |
| 5,352,813 A | * | 10/1994 | Cavell et al. .................. 556/21 |
| 6,482,958 B2 | * | 11/2002 | Junghans et al. .............. 549/6 |

FOREIGN PATENT DOCUMENTS

| EP | 1 099 681 A2 | 5/2001 |
| EP | 1 099 681 A3 | 1/2003 |
| WO | WO 02/10133 A1 | 2/2002 |

* cited by examiner

*Primary Examiner*—Johann Richter
*Assistant Examiner*—Sudhakar Katakam
(74) *Attorney, Agent, or Firm*—Nixon & Vanderhye

(57) ABSTRACT

A process for the production of a carboxylic acid and/or the alcohol ester of a carboxylic acid by carbonylating an alcohol and/or a reactive derivative thereof with carbon monoxide employing as the carbonylation catalyst, cobalt, rhodium or iridium coordinated with a tridentate ligand.

41 Claims, No Drawings

CARBONYLATION PROCESS USING METAL-TRIDENTATE LIGAND CATALYSTS

This application is the U.S. National Phase of International Application PCT/GB04/001943, filed 5 May 2004, which designated the U.S. PCT/GB04/001943 claims priority to British Application No. 0311091.3 filed 14 May 2003. The entire content of these applications are incorporated herein by reference.

The present invention relates in general to a process for the liquid phase carbonylation of an alcohol and/or a reactive derivative thereof. In particular the present invention relates to the liquid phase carbonylation of an alcohol and/or a reactive derivative thereof in the presence of a catalyst comprising cobalt or rhodium or iridium coordinated with a tridentate ligand.

Preparation of carboxylic acids by rhodium-catalysed carbonylation processes is known and is described, for example, in EP-A-0632006 and U.S. Pat. No. 4,670,570.

EP-A-0632006 discloses a process for the liquid phase carbonylation of methanol or a reactive derivative thereof which process comprises contacting carbon monoxide with a liquid reaction composition comprising methanol or a reactive derivative thereof, a halogen promoter and a rhodium catalyst system comprising a rhodium component and a bidentate phosphorus-sulphur ligand, the ligand comprising a phosphorus dative centre linked to a sulphur dative or anionic centre by a substantially unreactive backbone structure comprising two connecting carbon atoms or a connecting carbon and a connecting phosphorus atom.

Preparation of carboxylic acids by iridium-catalysed carbonylation processes is known and is described, for example in EP-A-0786447, EP-A0643034 and EP-A-0752406.

EP-A-0643034 describes a process for the production of acetic acid by carbonylation of methanol or a reactive derivative thereof which process comprises contacting methanol or a reactive derivative thereof with carbon monoxide in a liquid reaction composition in a carbonylation reactor characterised in that the liquid composition comprises (a) acetic acid, (b) an iridium catalyst, (c) methyl iodide, (d) at least a finite quantity of water, (e) methyl acetate and (f) as promoter, at least one of ruthenium and osmium.

The use of bidentate chelating phosphorus or arsenic ligands in carbonylation processes is known, for example, from GB 2,336,154, U.S. Pat. No. 4,102,920 and U.S. Pat. No. 4,102,921.

GB 2,336,154 describes a process for the liquid-phase carbonylation of an alcohol and/or a reactive derivative thereof to produce a carboxylic acid in the presence of a bidentate ligand of formula $R^1R^2X—Z—YR^5R^6$, wherein X and Y are independently N, P, As, Sb or Bi, and Z is a divalent linking group.

U.S. Pat. No. 4,102,920 describes a process for the carbonylation of alcohols, esters, ethers and organo halides in the presence of a rhodium complex with a polydentate phosphine or arsenic chelating ligand. U.S. Pat. No. 4,102,921 describes a similar process in the presence of an iridium complex with a polydentate phosphine or arsenic chelating ligand.

However, although bidentate rhodium complexes show activity for carbonylation reactions to produce carboxylic acids, the bidentate ligands and associated complexes are often unstable and degrade during the reaction or in processing of the carbonylation product, for example in product separation stages.

In addition, carbonylation reactions to produce carboxylic acid usually require relatively high purity carbon monoxide, which has a significant cost associated with it. It would thus be desirable to use carbon monoxide of lower purity. In particular, it would be desirable to utilise carbon monoxide containing relatively high levels of hydrogen, such as hydrogen/carbon monoxide mixtures produced by the reforming of hydrocarbons. Such mixtures are generally known as syngas. However, in the carbonylation of methanol to produce acetic acid, the presence of hydrogen is known to result in the formation of undesirable liquid by-products such as acetaldehyde, ethanol and propionic acid. Propionic acid requires an expensive and energy intensive distillation column to separate it from the acetic acid product. Furthermore acetaldehyde can undergo a series of condensation and other reactions to yield, eventually, higher organic iodide compounds. Some of these materials, especially, for example, hexyl iodide, are difficult to remove by conventional distillation and further treatment steps may be necessary to achieve acetic acid of sufficient purity. EP-A-0849-251, which describes an iridium catalysed process for the carbonylation of methanol to acetic acid, states that the amount of hydrogen in the carbon monoxide feed is preferably less than 1 mol % and the hydrogen partial pressure in the reactor is preferably less than 1 bar. Similarly, EP-A-0 728 727, which describes a rhodium catalysed process for the carbonylation of methanol to acetic acid, states that the hydrogen partial pressure in the reactor is preferably less than 2 bar.

It has also been found that, using certain rhodium catalysts for methanol carbonylation, the presence of hydrogen in the carbon monoxide feed leads to the production of ethanol and acetaldehyde with only minor amounts of acetic acid being produced.

U.S. Pat. No. 4,727,200, for example, describes a process for the homologation of an alcohol by reaction with synthesis gas using a rhodium-containing catalyst system. The major product formed with a synthesis gas feed is ethanol, acetic acid being a relatively minor by-product.

Moloy et al. (Organometallics, 1989, 8, pp2883-2893) describe a process for the rhodium-catalysed reductive carbonylation of methanol utilising synthesis gas in the presence of a diphosphine ligand to produce high levels of acetaldehyde. Addition of ruthenium to the catalyst favours hydrogenation to produce ethanol.

Thus, there remains a need for an improved process for the production of carboxylic acids and/or the alcohol esters of carboxylic acids by the catalytic carbonylation of an alcohol and/or a reactive derivative thereof.

It has now been found that an improved process may be achieved by employing a catalyst comprising cobalt, rhodium or iridium coordinated with a tridentate ligand.

Advantageously, the catalyst comprising cobalt, rhodium or iridium coordinated with a tridentate ligand according to the present invention has been found to give improved carbonylation rates in the carbonylation of an alcohol with carbon monoxide compared to a catalyst comprising said metals coordinated with bidentate ligands. In addition, the metal-tridentate ligand complexes may have higher stability than metal-bidentate ligand complexes in the carbonylation process.

Accordingly, the present invention provides for a process for the production of a carboxylic acid and/or the alcohol ester of a carboxylic acid, which process comprises carbonylating an alcohol and/or a reactive derivative thereof with carbon monoxide in a liquid reaction composition in a carbonylation reactor, said liquid reaction composition comprising said alcohol and/or reactive derivative thereof, a carbonylation catalyst, an alkyl halide co-catalyst and, optionally, a finite concentration of water, characterised in that the catalyst comprises cobalt, rhodium or iridium coordinated with a tridentate ligand or mixtures thereof.

The present invention also provides use of a carbonylation catalyst comprising cobalt, rhodium or iridium coordinated with a tridentate ligand or mixtures thereof in a process for the production of a carboxylic acid and/or the alcohol ester of a carboxylic acid, which process comprises carbonylating an alcohol and/or a reactive derivative thereof with carbon monoxide in a liquid reaction composition in a carbonylation reactor, said liquid reaction composition comprising said catalyst, said alcohol and/or reactive derivative thereof, an alkyl halide co-catalyst and, optionally, a finite concentration of water.

The tridentate ligand has three coordinating groups through which the ligand coordinates to a cobalt or rhodium or iridium metal centre. The three coordinating groups may be represented as L1, L2 and L3. Preferably, L1, L2 and L3 are, independently, selected from co-ordinating groups containing P, As, Sb, O, N, S and carbene as the donor (coordinating) atom.

Preferably the tridentate ligand is represented by the formula L1 (R1)L2(R2)L3, wherein R1 and R2 are linking groups that link L1 to L2 and L2 to L3 respectively, which linking groups are independently selected from arylene, alkenyl and alkyl groups. The linking groups R1 and R2 may themselves form at least one cyclic structure comprising L2, which may be represented by the generic structure A below:

Structure A

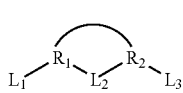

Preferably the tridentate ligand is represented by the formula L1 (R1)L2(R2)L3 as described above, and coordinates to the catalyst metal centre in a bridging conformation, such that two of L1 to L3, preferably L1 and L3, are mutually trans with respect to the metal centre. By mutually trans, as used throughout the specification, is meant that the angle formed by the two of the ligands and the metal centre, for example L1-M-L3, where M is the Co, Rh or Ir metal centre, is at least 145°, preferably at least 150°. The angles may be measured using conventional techniques, such as X-ray crystallography.

Preferably the tridentate ligand co-ordinates such that the donor atoms in the L1, L2 and L3 groups are in a meridional (mer-) co-ordination mode with respect to the metal centre. Preferably the tridentate ligand coordinates such that the donor atoms of the L1, L2 and L3 groups are in an essentially planar configuration with respect to the metal centre.

Preferably, at least two of L1 to L3 are independently selected from P, As and Sb containing groups. Where the tridentate ligand coordinates to the metal centre in a bridging conformation in which L1 and L3 are mutually trans, preferably at least L1 and L3 are P, As or Sb containing groups.

Most preferably L1 and L3 are P-containing groups and L2 is oxygen (O), and the tridentate ligand has the formula P1—R1—O—R2—P2, wherein P1 and P2 are phosphine-containing groups of general formula R3R4P and R5R6P, and wherein R3, R4, R5 and R6 are each independently selected from an alkenyl group, alkyl group, aryl group, especially phenyl, and substituted derivatives of said alkenyl, alkyl and aryl groups. Preferably R3, R4, R5 and R6 are each, independently, selected from a phenyl group. Each of the phenyl groups may be substituted or unsubstituted. Both P1 and P2 may be a diphenylphosphine group ($PPh_2$). Alternatively, one or more of the R3, R4, R5 and R6 phenyl groups in the P1 and P2 groups are substituted. Suitably, the phenyl groups may be substituted at one or more of the ortho positions by at least one group selected from alkyl, aryl and alkyloxy (OR) groups. Particularly preferred ortho substituents are Me, $CF_3$, Et, iso-Pr and OMe.

To improve the solubility of the tridentate ligand and hence the catalyst in the liquid reaction composition one or more of the R1, R2, R3, R4, R5 and R6 groups on the tridentate ligand may be substituted with one or more hydrophilic and/or polar groups. Examples of such groups include —$CO_2H$, —$CO_2Me$, —OH, —$SO_3H$, —$SO_3Na$, —$NH_2$, —$NH_3^+$ and —$NR_2H^+$.

Specific examples of suitable tridentate phosphine-containing ligands for use in the present invention include Xantphos, Thixantphos, Sixantphos, Homoxantphos, Phosxantphos, Isopropxantphos, Nixantphos, Benzoxantphos, DPEphos, DBFphos and R-Nixantphos, the structures 1-11 of which are given below. The R grouping of R-Nixantphos is preferably selected from alkyl and aryl groups, and is more preferably selected from methyl, ethyl, propyl and benzyl.

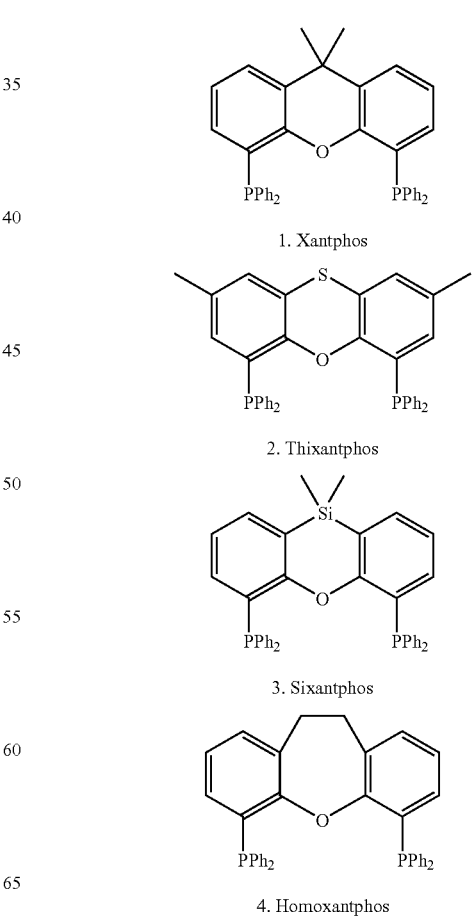

1. Xantphos

2. Thixantphos

3. Sixantphos

4. Homoxantphos

-continued

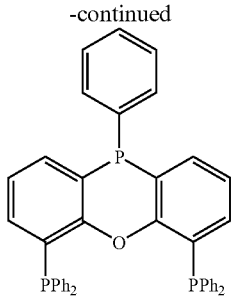

5. Phosxantphos

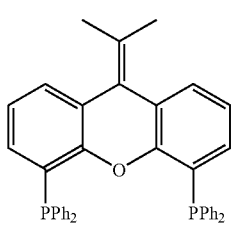

6. Isopropxantphos

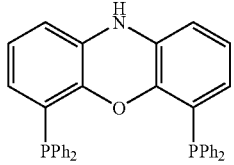

7. Nixantphos

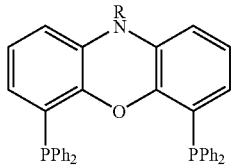

8. R-Nixantphos

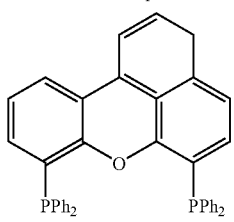

9. Benzoxantphos

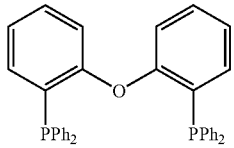

10. DPEphos

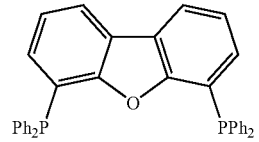

11. DBFphos

Suitably, structures 1 to 11 above, may be substituted by one or more substituents, such as one or more alkyl groups, for example t-Bu-Xantphos, the structure, 12, of which is given below.

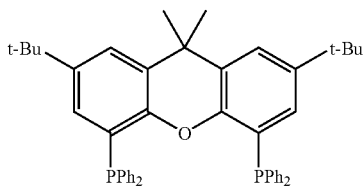

12. t-Bu-xantphos

In the tridentate phosphine-containing ligands represented by structures 1-12 above, the diphenylphosphine groups may be replaced by P1 and P2 groups as previously defined above. In particular, preferred P1 and P2 groups are R3R4P and R5R6P groups wherein R3, R4, R5 and R6 are each, independently selected from phenyl groups and substituted phenyl groups and one or more of the R3, R4, R5 and R6 groups are substituted, preferably at one or more of the ortho positions, with alkyl, aryl or alkyloxy (OR) groups. Particularly preferred ortho substituents are Me, $CF_3$, Et, iso-Pr and OMe.

To improve the solubility of the tridentate ligands represented by structures 1 to 12, and thus the catalyst, in the liquid reaction composition, the tridentate ligands may be substituted with one or more hydrophilic and/or polar groups, especially on one or more of the phosphine groups on the tridentate ligand. Examples of such groups include $-CO_2H$, $-CO_2Me$, $-OH$, $-SO_3H$, $-SO_3Na$, $-NH_2$, $-NH_3^+$ and $-NR_2H^+$.

Suitably, the phosphine containing ligands of any of the structures 1 to 12, and substituted variants thereof as described above, may have the O atom in L2 substituted by a sulphur atom (S) or a nitrogen atom (N).

Preferred tridentate arsine- and stibine-containing ligands include structures 1 to 12 above, or variants thereof as described, wherein the phosphorus atoms are replaced by arsenic or antimony atoms. Preferred mixed tridentate ligands include structures 1 to 12 above, or variants thereof as described, comprising, as L1 and L3, a combination of two groups selected from phosphorus, arsenic and antimony-containing groups.

For example, the structures of As, As- t-Bu-xantphos and P, As-t-Bu-xantphos are given below:

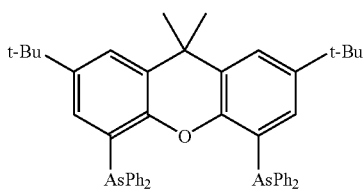

13. As, As-t-Bu-xantphos

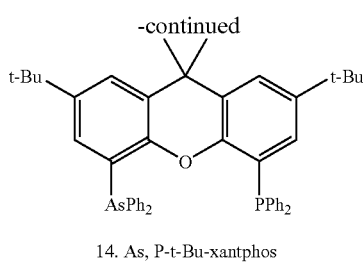

14. As, P-t-Bu-xantphos

The tridentate ligands may be synthesized according to methods known in the art and/or are commercially available. More specifically, the ligands represented by structures 1 to 14, and variants thereof as described, may be synthesized according to methods as described or analogous to those described by van der Veen et al., Chem. Commun., 2000, 333, the contents of which are herein incorporated by reference.

The catalyst in the process of the present invention is a cobalt, rhodium or iridium catalyst, preferably a rhodium or iridium catalyst, and most preferably, a rhodium catalyst.

The catalyst of the present invention may be prepared by coordinating an iridium-, rhodium- or cobalt-containing compound with the tridentate ligand. The catalyst may be formed in situ in the liquid reaction composition, by separately adding an iridium-, rhodium- or cobalt-containing compound, and the tridentate ligand to the liquid reaction composition. The iridium-, rhodium- or cobalt-containing compound can be added in any suitable form which dissolves in the liquid reaction composition or is convertible to a soluble form. Preferably, however, the catalyst is added to the liquid reaction composition in the form of a pre-formed metal-tridentate ligand complex in which the tridentate ligand is coordinated to the iridium-, rhodium- or cobalt-containing compound. The pre-formed metal-tridentate ligand complex may be prepared, for example, by mixing a suitable iridium-, rhodium- or cobalt-containing compound having displaceable groups with the tridentate ligand in a suitable solvent, for example methanol, prior to addition to the liquid reaction composition.

Examples of pre-formed iridium-tridentate ligand complexes include [{L1(R1)L2(R2)L3}Ir(COMe)I$_2$], [{L1(R1)L2(R2)L3}Ir(CO)I], [{L1(R1)L2(R2)L3}Ir(CO)]$^+$ and [{L1(R1)L2(R2)L3}IrI(CO)Me]$^+$, wherein L1 (R1)L2(R2)L3 represents the tridentate ligand as previously described.

Examples of pre-formed rhodium-tridentate ligand complexes include [{L1(R1)L2(R2)L3}Rh(COMe)I$_2$], [{L1(R1)L2(R2)L3}Rh(CO)I], [{L1(R1)L2(R2)L3}Rh(CO)]$^+$ and [{L1(R1)L2(R2)L3}RhI(CO)Me]$^+$, wherein L1(R1)L2(R2)L3 represents the tridentate ligand as previously described, for example [{Xantphos}Rh(COMe)I$_2$].

Preferably the iridium-, rhodium-, or cobalt-containing compound is a chloride free compound, such as an acetate, which is soluble in one or more of the liquid reaction composition components, and so may be added to the reaction as a solution therein.

Examples of suitable iridium-containing compounds include IrCl$_3$, IrI$_3$, IrBr$_3$,[Ir(CO)$_2$I]$_2$, [Ir(CO)$_2$Cl]$_2$, [Ir(CO)$_2$Br]$_2$, [Ir(CO)$_4$I$_2$]$^-$H$^+$, [Ir(CO)$_2$Br$_2$]$^-$H$^+$, [Ir(CO)$_2$I$_2$]$^-$H$^+$, [Ir(CH$_3$)I$_3$(CO)$_2$]$^-$H$^+$, Ir$_4$(CO)$_{12}$, IrCl$_3$.4H$_2$O, IrBr$_3$.4H$_2$O, Ir$_3$(CO)$_{12}$, iridium metal, Ir$_2$O$_3$, IrO$_2$, Ir(acac)(CO)$_2$, Ir(acac)$_3$, iridium acetate, [Ir$_3$O(OAc)$_6$(H$_2$O)$_3$][OAc], and hexachloroiridic acid H$_2$[IrCl$_6$], preferably, chloride-free complexes of iridium such as acetates, oxalates and acetoacetates.

Examples of suitable rhodium-containing compounds include [Rh(CO)$_2$Cl]$_2$, [Rh(CO)$_2$I]$_2$, [Rh(Cod)Cl]$_2$, rhodium (III) chloride, rhodium (III) chloride trihydrate, rhodium (III) bromide, rhodium (III) iodide, rhodium (III) acetate, rhodium dicarbonylacetylacetonate, RhCl(PPh$_3$)$_3$ and RhCl(CO)(PPh$_3$)$_2$.

Examples of suitable cobalt-containing compounds include CoI$_2$, CoCl$_2$ hexahydrate, Co(acac)$_3$, Co$_2$(CO)$_8$, Co$_4$(CO)$_{12}$, Co(acetate)$_2$ tetrahydrate and [Co(CO)$_4$].

Preferably, the concentration of iridium in the liquid reaction composition is in the range 100 to 6000 ppm by weight of iridium, more preferably in the range 400 to 5000 ppm, such as in the range 500 to 3000 ppm by weight.

Preferably, the concentration of rhodium in the liquid reaction composition is in the range 25 to 5000 ppm by weight of rhodium, more preferably, in the range 250 to 3500 ppm.

Preferably, the concentration of cobalt in the liquid reaction composition is in the range 25 to 5000 ppm by weight of cobalt, more preferably, in the range 250 to 3500 ppm.

The mole ratio of the cobalt or rhodium or iridium metal to the tridentate ligand in the reactor is optimally approximately 1:1, especially where a pre-formed metal-tridentate ligand complex is employed. Alternatively, an excess of ligand may be present in the liquid reaction composition, especially, for example, where the metal-tridentate ligand complex is to be formed in-situ. Thus, the mole ratio of the cobalt or rhodium or iridium metal to the tridentate ligand may be less than 1:1, suitably in the range from 1:1 to 1:2.

The liquid reaction composition may also comprise a promoter metal. Suitable promoters are selected from ruthenium, osmium, rhenium, cadmium, mercury, zinc, gallium, indium and tungsten. Preferred promoters are selected from osmium and ruthenium, most preferably, ruthenium. The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, [Ru(CO)$_3$I$_3$]—H+, [Ru(CO)$_2$I$_2$]$_n$, [Ru(CO)$_4$I$_2$], [Ru(CO)$_3$I$_2$]$_2$, tetra(aceto)chlororuthenium(II,III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (III) dimer, dibromotricarbonylruthenium (II) dimer, and other organoruthenium complexes such as tetrachlorobis(4-cymene)diruthenium(II), tetrachlorobis(benzene)diruthenium(II), dichloro(cycloocta-1,5diene) ruthenium (II) polymer and tris(acetylacetonate)ruthenium (III).

Examples of suitable osmium-containing compounds which may be used as sources of promoter include osmium (M) chloride hydrate and anhydrous, osmium metal, osmium tetraoxide, triosmiumdodecacarbonyl, [Os(CO)$_4$I$_2$], [Os(CO)$_3$I$_2$]$_2$, [Os(CO)$_3$I$_3$]—H+, pentachloro-µ-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3 \cdot xH_2O$, $[Re(CO)_4I_2]$, $Re(CO)_4I_2]^-H^+$ and $ReCl_5 \cdot yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used include $Hg(OAc)_2$, $HgI_2$, $HgBr_2$, $HgCl_2$, $Hg_2I_2$, and $Hg_2Cl_2$.

Examples of suitable zinc-containing compounds which may be used include $Zn(OAc)_2$, $Zn(OH)_2$, $ZnI_2$, $ZnBr_2$, $ZnCl_2$, and zinc acetylacetonate.

Examples of suitable gallium-containing compounds which may be used include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used include indium acetylacetonate, indium acetate, $InCl_3$, $InBr_3$, $InI_3$ and $In(OH)_3$.

Examples of suitable tungsten-containing compounds which may be used include $W(CO)_6$, $WCl_4$, $WCl_6$, $WBr_5$, $WI_2$, $C_9H_{12}W(CO)_3$ and any tungsten chloro-, bromo-, or iodo-carbonyl compound.

Preferably, the promoter is present in an effective amount up to the limit of its solubility in the liquid reaction composition and/or any liquid process streams recycled to the carbonylation reactor from the carboxylic acid recovery stage. The promoter is suitably present in the liquid reaction composition at a molar ratio of promoter to iridium, rhodium or cobalt of 0.1:1 to 20:1, preferably 0.5:1 to 10:1, more preferably 2:1 to 10:1. A suitable promoter concentration is less than 8000 ppm, such as 400 to 7000 ppm.

The liquid reaction composition may also comprise an effective amount of a stabiliser and/or promoter compound selected from alkali metal iodides, alkaline earth metal iodides, metal complexes capable of generating I—, salts capable of generating I—, and mixtures of two or more thereof. Examples of suitable alkali metal iodides include lithium iodide, sodium iodide and potassium iodide, preferably lithium iodide. Suitable alkaline earth metal iodides include calcium iodide. Suitable metal complexes capable of generating I— include complexes of the lanthanide metals, for example, samarium and gadolinium, cerium, and other metals such as molybdenum, nickel, iron, aluminium and chromium. Salts capable of generating I— include, for example, acetates which are capable of conversion in-situ to I— typically LiOAc and organic salts, such as quaternary ammonium iodides and phosphonium iodides, which may be added as such.

Suitably, the amount of compound used is such that it is effective in providing an increase in the solubility of the catalyst and, preferably, does not significantly decrease the carbonylation reaction rate.

Corrosion metals, such as chromium, iron and molybdenum, which may have an adverse affect on the reaction rate, may be minimised by using suitable corrosion resistant materials of construction. Corrosion metal and other ionic impurities may be reduced by the use of a suitable ion exchange resin bed to treat the liquid reaction composition, or preferably a catalyst recycle stream. Such a process is described in U.S. Pat. No. 4,007,130.

The alkyl halide co-catalyst may suitably be a lower, e.g. $C_1$ to $C_4$, alkyl halide. Preferably the alkyl halide is an alkyl iodide, such as methyl iodide. The concentration of alkyl halide co-catalyst in the liquid reaction composition is suitably in the range of from 1 to 30% by weight, for example from 1 to 20% by weight.

In the process of the present invention, a reactant chosen from an alcohol and/or a reactive derivative thereof is carbonylated with carbon monoxide to produce a carboxylic acid and/or the alcohol ester of a carboxylic acid.

A suitable alcohol reactant is any alcohol having from 1 to 20 carbon atoms and at least one hydroxyl group. Preferably the alcohol is a monofunctional aliphatic alcohol, preferably having from 1 to 8 carbon atoms. Most preferably the alcohol is methanol, ethanol and/or propanol. A mixture comprising more than one alcohol may be used. The carbonylation product of the alcohol will be a carboxylic acid having one carbon atom more than the alcohol and/or an ester of the alcohol and the carboxylic acid product. A particularly preferred alcohol is methanol, the carbonylation product of which is acetic acid and/or methyl acetate.

Suitable such reactive derivatives of an alcohol include esters, halides and ethers.

A suitable ester reactant is an ester of an alcohol and a carboxylic acid. Preferably the ester reactant is an ester of a carboxylic acid and an alcohol which alcohol has from 1 to 20 carbon atoms. More preferably the ester reactant is an ester of a carboxylic acid and a monofunctional aliphatic alcohol which alcohol has from 1 to 8 carbon atoms. Most preferably the ester reactant is an ester of a carboxylic acid and methanol, ethanol or propanol. Preferably the ester reactant is an ester of an alcohol and the carboxylic acid product. Preferably the ester reactant has up to 20 carbon atoms. A mixture of ester reactants may be used. The carboxylic acid carbonylation product of the ester reactant will be a carboxylic acid having one carbon atom more than the alcohol component of the ester reactant. A particularly preferred ester reactant is methyl acetate, the carbonylation product of which is acetic acid.

A suitable halide reactant is any hydrocarbyl halide having up to 20 carbon atoms. Preferably the halide reactant is an iodide or a bromide. More preferably the halide component of the hydrocarbyl halide reactant is the same halide as that of the alkyl halide co-catalyst. Most preferably the hydrocarbyl halide is a hydrocarbyl iodide, most preferably methyl iodide, ethyl iodide or propyl iodide. A mixture of hydrocarbyl halide reactants may be used. The carboxylic acid product of the hydrocarbyl halide reactant will be a carboxylic acid having one more carbon atom than the hydrocarbyl halide reactant. The ester carbonylation product of the hydrocarbyl halide will be the ester of the hydrocarbyl halide and a carboxylic acid having one more carbon atom than the hydrocarbyl halide.

A suitable ether reactant is any hydrocarbyl ether having up to 20 carbon atoms. Preferably the ether reactant is a dialkyl ether, most preferably dimethyl ether, diethyl ether or dipropyl ether. A mixture of ethers may be used. The carbonylation products of the ether reactant will be carboxylic acids having one carbon atom more than each of the hydrocarbyl groups of the ether and/or ester derivatives thereof. A particularly preferred ether reactant is dimethyl ether, the carboxylic acid product of which is acetic acid.

A mixture of alcohol, ester, halide and ether reactants may be used in the carbonylation process. More than one alcohol, ester, halide and/or ether may be used. A particularly preferred reactant is methanol and/or methyl acetate, the carboxylic acid carbonylation products of which are acetic acid.

The liquid reaction composition may be anhydrous but preferably comprises a finite concentration of water. By anhydrous as used herein is meant that the liquid reaction composition is essentially free of water, such that the liquid reaction composition comprises less than 0.1 wt % water. By finite concentration of water, as used herein, meant that the liquid reaction composition comprises at least 0.1 wt % water. Preferably, water may be present at a concentration in the range from 0.1 to 30%, for example from 1 to 15%, and more preferably from 1 to 10%, by weight based on the total weight of the liquid reaction composition. Water may be added to the liquid reaction composition, where desired, or may be formed in situ in the carbonylation reaction. For example, in the carbonylation of methanol, water may be formed by the esterification reaction between methanol reactant and acetic acid product.

The water may be introduced in to the carbonylation reactor together with or separately from the other reactants such as esters, for example methyl acetate. Water may be separated from the liquid reaction composition withdrawn from the reactor and recycled in controlled amounts to maintain the required concentration in the liquid reaction composition.

The carboxylic acid product, for example, acetic acid may be present as a solvent in the liquid reaction composition of the present invention.

The carbon monoxide for use in the present invention may be essentially pure or may contain inert impurities such as carbon dioxide, methane, nitrogen, noble gases, water and $C_1$ to $C_4$ paraffinic hydrocarbons. The carbon monoxide may also be obtained from commercial sources, such as the reforming of hydrocarbons which produce a mixture of carbon monoxide, carbon dioxide and hydrogen. The carbon monoxide may be fed to the reaction zone, therefore, as mixture of carbon monoxide, hydrogen and/or carbon dioxide.

The partial pressure of carbon monoxide in the carbonylation reaction may suitably be in the range from 1 to 70 barg.

The carbonylation reaction may be carried out at a total pressure in the range from 10 to 100 barg. The temperature may suitably be in the range from 50 to 250° C., typically from 120 to 200° C.

The process may be operated batchwise or continuously, preferably continuously.

The carboxylic acid product may be recovered from the liquid reaction composition by withdrawing vapour and/or liquid from the carbonylation reactor and recovering carboxylic acid from the withdrawn material. Preferably, carboxylic acid is recovered from the liquid reaction composition by continuously withdrawing liquid reaction composition from the carbonylation reactor and recovering carboxylic acid from the withdrawn liquid reaction composition by one or more flash and/or fractional distillation stages in which the acid is separated from the other components of the liquid reaction composition such as cobalt or rhodium or iridium catalyst, alkyl halide co-catalyst, optional promoter, carboxylic acid ester, unreacted alcohol, optional water and carboxylic acid solvent, which may be recycled to the reactor.

The use of a catalyst that comprises cobalt, rhodium or iridium coordinated with a tridentate ligand according to the present invention has also been found to give improved selectivity to carboxylic acid products and reduced selectivity to liquid hydrogenation by-products, such as alcohols and aldehydes, in the presence of hydrogen. In a conventional process for the production of a carboxylic acid, a purge is usually taken to keep the hydrogen at low partial pressure in the reactor (the hydrogen builds up due to impurity levels in the carbon monoxide feed and hydrogen formed in situ). Since only low levels of hydrogen can be tolerated, the purge often contains low levels of hydrogen and significant levels of carbon monoxide, which is disposed of. Since it has now been found that the process of the present invention can be operated with higher levels of hydrogen in the reactor, the purge stream will contain higher levels of hydrogen and so significantly less carbon monoxide need be purged from the reactor, thereby improving overall CO yield.

A further advantage of the process of the present invention is that high selectivity to the desired liquid products can be achieved in the presence of hydrogen, allowing carbon monoxide feed streams with higher contents of hydrogen to be employed in the carbonylation process. This has significant cost savings. In particular, utilising a carbon monoxide feed with greater than 1 mol % $H_2$ allows less expensive, non-cryogenic, methods of syngas separation to be employed, such as membrane separation technologies.

Accordingly, in a further aspect, the present invention provides a process for the production of a carboxylic acid and/or the alcohol ester of a carboxylic acid which process comprises carbonylating an alcohol and/or a reactive derivative thereof with carbon monoxide in a liquid reaction composition in a carbonylation reactor, said liquid reaction composition comprising said alcohol and/or reactive derivative thereof, a carbonylation catalyst, an alkyl halide co-catalyst, and, optionally, a finite concentration of water, wherein the catalyst comprises cobalt, rhodium or iridium co-ordinated with a tridentate ligand or mixtures thereof, and wherein there is also maintained in the carbonylation reactor, hydrogen at a hydrogen:CO ratio of at least 1:100 and/or wherein carbon monoxide is fed to the carbonylation reactor as a feedstream containing at least 1 mol % hydrogen.

Hydrogen may be fed to the reactor separately to the carbon monoxide feed, but is preferably fed as a mixture with carbon monoxide. Where the feed comprises a mixture of carbon monoxide and hydrogen, the feed contains at least 1 mol % hydrogen, such as at least 2 mol % hydrogen and, more preferably, at least 5 mol % hydrogen. The hydrogen to CO mole ratio in the feed is most preferably between 1:100 and 10:1, such as 1:20 to 5:1. The reactor may be fed directly with a source of carbon monoxide obtained from a commercial source, such as the reforming of hydrocarbons in a syngas unit (for example, a partial oxidation reactor, steam reformer and/or an autothermal reformer) to produce a mixture of CO, hydrogen and $CO_2$ (syngas), which syngas typically comprises hydrogen to CO at a mole ratio of 5:1 to 1.5:1.

Where hydrogen is fed to the reactor with CO, the CO consumption in the reactor causes the molar ratio of hydrogen to CO in the reactor to be generally higher than the molar ratio of hydrogen to CO in the feed to the reactor. In addition to hydrogen fed to the reaction, hydrogen also may be produced in-situ by the water-gas shift reaction. Thus, where hydrogen is present in the feed to the reactor, and particularly for a carbonylation process operated at high CO conversion, such as a batch process, the level of CO in the reactor may become quite low, and the molar ratio of hydrogen to CO in the reactor may get correspondingly high, such as 100:1 or higher. Preferably, however, the hydrogen to CO molar ratio in the reactor is maintained at less than 100:1. The molar ratio of hydrogen to CO in the reactor may be at least 1:100, such as, at least 1:10, and more preferably at least 1:1. The hydrogen partial pressure in the reactor is preferably greater than 1 bar, most preferably greater than 2 bar.

The invention will now be illustrated by way of example only and with reference to the following examples:

EXAMPLES

The carbonylation reactions of Comparative Examples A and B, and Example 1 were conducted in the absence of hydrogen whilst Comparative Examples C, D and E, and Examples 2 to 4 were carried out in the presence of hydrogen.

General Reaction Method A

Methyl acetate, methyl iodide, dppe (dppe=bis-1,2-diphenylphosphinoethane) and [{Rh(CO)$_2$Cl}$_2$] were obtained from Aldrich. Xantphos was obtained from Strem Chemicals. Experiments were performed using a 300 ml zirconium autoclave equipped with a magnetically driven stirrer with a gas dispersion impeller system, liquid catalyst injection facility and cooling coils. The gas supply to the autoclave was provided from a ballast vessel, feed gas being provided to maintain the autoclave at a constant pressure during reaction. The rate of gas uptake was used to calculate the carbonylation rate, as number of moles of reactant consumed per litre of reactor composition per hour {mol l$^{-1}$ hr$^{-1}$}, at a particular reactor composition (reactor composition based on a cold degassed volume). The methyl acetate concentration was calculated during the course of the reaction from the starting composition, assuming that one mole of methyl acetate is consumed for every mole of carbon monoxide that is consumed. No allowance was made for organic components in the autoclave headspace.

Comparative Example A

This experiment demonstrates the carbonylation of methanol by a rhodium catalyst in the absence of a tridentate ligand.

0.151 g of [{Rh(CO)$_2$Cl}$_2$] catalyst was dissolved in a portion of an acetic acid charge, and charged to the liquid injection facility. The reactor was then pressure tested with nitrogen, vented via a gas sampling system, and flushed with carbon monoxide several times. The desired quantities of the remaining liquid components (methyl acetate, remaining acetic acid charge, water and methyl iodide) of the liquid reaction composition were charged to the autoclave via a liquid addition port. The autoclave was then pressurised with 5 barg of carbon monoxide and slowly vented. The autoclave was then pressurised with carbon monoxide (approximately 5 barg) and heated with stirring (1500 r.p.m.) to a reaction temperature of 190° C. The total pressure was then raised to approximately 3 barg below the desired operating pressure by feeding carbon monoxide from the ballast vessel. Once stable at temperature (about 15 minutes) the catalyst was injected using an over pressure of carbon monoxide. The catalyst injection facility has an efficiency of >90%. The reactor pressure was maintained at a constant value (±0.5 barg) by feeding gas from the ballast vessel throughout the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) control system. In addition, excess heat of reaction was removed by means of the cooling coils. The experiment was continued until the gas uptake ceased. The ballast vessel was then isolated and the reactor cooled rapidly by use of the cooling coils. The charge compositions are given in Table 1. The carbonylation rate data obtained is given in Table 2. The acetic acid obtained contained very low amounts of propionic acid and its precursors.

Comparative Example B

This experiment demonstrates the carbonylation of methanol by a rhodium dppe based catalyst. Dppe is an example of a bidentate phosphine ligand.

In this experiment, a pre-formed diphosphine based rhodium catalyst was used. 0.71 g of [(dppe)RhI$_3$(CO)] was placed in the autoclave and covered with a portion of the acetic acid charge (approx. 10 g). The MeI co-catalyst was placed in the liquid injection facility along with a small amount of acetic acid (ca. 3 g). The experiment was then conducted in accordance with Comparative Example A above. The charge compositions used are shown in Table 1. The carbonylation rate data obtained is shown in Table 2.

Example 1

This example demonstrates the carbonylation of methanol by a rhodium Xantphos based catalyst.

In this example, the phosphine-rhodium complex was formed in situ. 0.151 g of [{Rh(CO)$_2$Cl}$_2$] catalyst and 0.45 g of Xantphos ligand were placed in the autoclave and covered with a portion of the acetic acid charge (approx. 10 g) prior to the pressure test. The MeI co-catalyst was placed in the liquid injection facility along with a small amount of acetic acid (ca. 3 g). The experiment was then conducted as for Comparative Example A above. The charge compositions used are given in Table 1. The carbonylation rate data obtained is given is Table 2.

TABLE 1

| Ex. | MeOAc/g | AcOH/g | MeI/g | Water/g | [{Rh(CO)$_2$Cl}$_2$]/g | Additive or complex | Amount of additive/complex/g |
|---|---|---|---|---|---|---|---|
| A | 30.05 | 79.20 | 22.62 | 18.08 | 0.151 | — | — |
| B | 30.03 | 78.68 | 22.60 | 18.50 | — | [(dppe)RhI$_3$(CO)] | 0.71 |
| 1 | 30.02 | 78.98 | 22.65 | 18.09 | 0.151 | Xantphos | 0.45 |

TABLE 2

| Example | Catalyst | Water/% w/w | Rate/mol l$^{-1}$ hr$^{-1}$ @15% MeOAc | Water/% w/w | Rate/mol l$^{-1}$ hr$^{-1}$ @10% MeOAc |
|---|---|---|---|---|---|
| A | Rh only | 10.7 | 13.0 | 9.4 | 12.9 |
| B | Rh/dppe | 11.0 | 5.2 | 9.6 | 4.5 |
| 1 | Rh/Xantphos | 10.7 | 15.7 | 9.4 | 14.8 | a) All reactions at 28 barg total pressure and 190° C. with a stirrer speed of 1500 r.p.m..

From an inspection of Table 2 it can clearly be seen that in comparison with Comparative Example B, the use in Example 1 of a rhodium catalyst modified by Xantphos (a tridentate ligand) shows a substantial increase in rate when the compared to the bidentate ligand used in Comparative Example B. Comparison of Example 1 with Comparative Example A shows an increase in rate using a tridentate ligand compared to the rate obtained using an unmodified rhodium catalyst.

General Reaction Method B

Methanol, methyl iodide, RuCl$_3$.hydrate and dppp (dppp=bis-1,3-diphenylphosphinopropane) were obtained from Aldrich. The (acac)Rh(CO)$_2$ and Xantphos were obtained from Strem Chemicals. RuCl$_3$ was obtained from Johnson Matthey. Experiments were performed using a 300 ml zirconium autoclave equipped with a magnetically driven stirrer with a gas dispersion impeller system, liquid catalyst injection facility and cooling coils. The gas supply to the autoclave was provided from a ballast vessel, feed gas being provided to maintain the autoclave at a constant pressure during reaction.

Comparative Example C

This experiment demonstrates the reaction of methanol with carbon monoxide in the presence of hydrogen by a rhodium catalyst in the presence of dppp and a ruthenium promoter during a 2 hour run time. Dppp is a bidentate phosphine ligand. A mixture of hydrogen and carbon monoxide at a H$_2$:CO ratio of 2:1 was used. 2.031 gram of (dppp)Rh(COMe)I$_2$ and 2.115 gram of RuCl$_3$ were suspended in a portion of the methanol charge and charged to the autoclave. The reactor was then pressure tested with nitrogen, vented via a gas sampling system, and flushed with synthesis gas three times. The remaining liquid components of the reaction composition (the remaining methanol and methyl iodide) were charged to the autoclave via a liquid addition port. The autoclave was then pressurised with 5 barg of synthesis gas and slowly vented. The autoclave was then pressurised with synthesis gas (approximately 20 barg) and heated with stirring (1220 r.p.m.) to reaction temperature, 140° C. Once stable at temperature (about 15 minutes), the total pressure was raised to the desired operating pressure by feeding synthesis gas from the ballast vessel. The reactor pressure was maintained at a constant value (±0.5 barg) by feeding gas from the ballast vessel throughout the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) control system. After a suitable time, T, (see Table 3b), the ballast vessel was isolated and the reactor rapidly cooled by use of the cooling coils. Charge composition data is given in Table 3a and reaction conditions in Table 3b. The product distribution obtained is given in Table 4 and product selectivity data is given in Table 5.

Comparative Example D

This experiment demonstrates the reaction of methanol with carbon monoxide in the presence of hydrogen by a rhodium catalyst in the presence of dppp and a ruthenium promoter during a 30 min run time. A mixture of hydrogen and carbon at a H$_2$:CO ratio of 2:1 was used. In this experiment the phosphine-rhodium complex was generated in situ. 1.114 gram of dppp was placed in a portion of the methanol charge (ca. 60 g) with 0.658 gram of (acac)Rh (CO)$_2$ to form a catalyst precursor suspension. 2.590 gram of RuCl$_3$.3H$_2$O was placed in the autoclave together with approximately 5 gram of methanol and the autoclave was pressure tested. The MeI co-catalyst was added to the autoclave, followed by the catalyst precursor suspension. The remaining methanol was added and the autoclave was pressurised with syngas (approximately 20 barg). The experiment was then conducted as for Comparative Example C. Charge composition data and reaction conditions are shown in Tables 3a and 3b respectively. The product distribution and product selectivity data obtained is given in Tables 4 and 5 respectively.

Comparative Example E

This experiment demonstrates the reaction of methanol with carbon monoxide in the presence of hydrogen by a rhodium catalyst in the presence of dppp, but in the absence of a ruthenium promoter, during a 2 hour run time. A mixture of hydrogen and carbon at a $H_2$:CO ratio of 2:1 was used. The reaction was performed according to the method of Comparative Example D using the charge composition and reaction conditions as detailed in Tables 3a and 3b respectively. Product distribution and product selectivity data is given in Tables 4 and 5 respectively.

Example 2

This example demonstrates the reaction of methanol with carbon monoxide in the presence of hydrogen by a rhodium Xantphos based catalyst in the presence of a ruthenium promoter. A mixture of hydrogen and carbon at a $H_2$:CO ratio of 2:1 was used. In this experiment the phosphine-rhodium complex was generated in situ. 1.571 gram of Xantphos was placed in a portion of the methanol charge (ca. 60 g) with 0.646 gram of (acac)Rh(CO)$_2$ and 2.084 gram of RuCl$_3$ to form a catalyst precursor suspension. The MeI co-catalyst was added to the catalyst injection system along with a small amount of methanol (5 gram). The catalyst precursor suspension was added to the autoclave, followed by the remaining methanol and the autoclave was pressurised with syngas (approximately 20 barg). The experiment was then conducted as for Comparative Example C, using the charge composition and reaction conditions as detailed in Tables 3a and 3b respectively. The product distribution data obtained is given is Table 4 and product selectivity data is given in Table 5.

Example 3

This example demonstrates the reaction of methanol with carbon monoxide in the presence of hydrogen by a rhodium Xantphos based catalyst, and in the absence of a ruthenium promoter. A mixture of hydrogen and carbon at a $H_2$:CO ratio of 2:1 was used. The reaction was performed according to the method of Comparative Example E using the charge composition and reaction conditions as detailed in Tables 3a and 3b respectively. The product distribution data obtained is given is Table 4 and the selectivity data obtained is shown in Table 5.

TABLE 3b

| Example | Reaction temperature T(° C.) | Reaction pressure P(bar) | Reaction Time/ mins | Pressure drop (bar) |
|---|---|---|---|---|
| C | 140 | 67 | 120 | 61.8 |
| D | 140 | 67 | 30 | 13.4 |
|  |  |  |  | (26.8*) |
| E | 140 | 70 | 120 | 17.9 |
| 2 | 140 | 68.7 | 17 | 5.8 |
| 3 | 140 | 68.4 | 21 | 7.3 |

*Experiment in different autoclave with larger ballast vessel, recalculated gas uptake 26.8bar may be compared to the other experiments

TABLE 4

| Example | MeOH % w/w | AcOH % w/w | MeOAc % w/w | EtOH % w/w | Et$_2$O % w/w | EtOMe % w/w | Me$_2$O % w/w | AcH % w/w |
|---|---|---|---|---|---|---|---|---|
| C | 28.6 | 1.1 | 4.5 | 14.2 | 0.4 | 3.5 | 8.2 | 0.9 |
| D | 54.0 | 0.3 | 3.7 | 5.3 | 0.1 | ND | 7.7 | 1.9 |
| E | 35.1 | 0.4 | 2.8 | <0.05 | 0.1 | <0.05 | 10.8 | 3.1 |
| 2 | 51.7 | 0.9 | 14.15 | 0.1 | 0.0 | 0.8 | 2.9 | 0.1 |
| 3 | 50.8 | 1.0 | 15.4 | 0.0 | 0.0 | 0.0 | 4.1 | 0.1 |

TABLE 5

| Example | MeOH conversion %$^{(a)}$ | EtOH and Derivatives %$^{(b)}$ | AcOH and Derivatives %$^{(c)}$ | AcH %$^{(d)}$ | CH$_4$ %$^{(e)}$ |
|---|---|---|---|---|---|
| C | 40.5 | 66.4 | 15.7 | 3.4 | 14.4 |
| D | 16.8 | 42.7 | 20.0 | 15.3 | 21.9 |
| E | 38.8 | 1.2 | 28.1 | 42.9 | 26.9 |

TABLE 3a

| Example | Additive | Additive/g | Complex/g | (acac)Rh(CO)$_2$/g | RuCl$_3$/g | MeOH/g | MeI/g |
|---|---|---|---|---|---|---|---|
| C |  |  | 2.031 [(dppp)RhAcI$_2$] | 0 | 2.115 | 80.05 | 14.50 |
| D | Dppp | 1.114 |  | 0.658 | 2.590(*) | 79.35 | 14.36 |
| E | Dppp | 1.215 |  | 0.637 | 0 | 79.75 | 14.58 |
| 2 | Xantphos | 1.571 |  | 0.646 | 2.084 | 79.48 | 14.58 |
| 3 | Xantphos | 1.571 |  | 0.651 | 0 | 78.47 | 14.49 |

(*)(H$_2$O)$_3$RuCl$_3$ used as the ruthenium source

TABLE 5-continued

| Example | MeOH conversion %[a] | EtOH and Derivatives %[b] | AcOH and Derivatives %[c] | AcH %[d] | CH$_4$ %[e] |
|---|---|---|---|---|---|
| 2 | 31.1 | 2.6 | 35.7 | 0.5 | 60.7 |
| 3 | 29.2 | 0 | 38.3 | 0.3 | 60.9 |

[a] Methanol conversion was calculated from the recovered methanol in the liquid product (Conversion % = 100 * (moles MeOH$_{init}$ − moles MeOH$_{recov}$)/moles MeOH$_{init}$). Typical mass balance is of the order of 80-90%, the main loss being that of volatile DME on venting the autoclave. For the purpose of calculation DME and the OMe groups in the compounds MeOEt, MeOAc and Dimethoxyethane are considered as unreacted methanol.
[b] The selectivity to ethanol and derivatives was based on the sum of the selectivity to EtOH and the ethyl groups in, Et$_2$O, MeOEt and EtOAc in the total liquid products recovered.
[c] The selectivity to acetic acid and derivatives was based on the sum of the selectivity to acetic acid and the acetate groups in AcOH, MeOAc and EtOAc in the total liquid products recovered.
[d] The selectivity acetaldehyde and derivatives was based on the sum of the selectivity to acetaldehyde and the ethylidene group in dimethoxyethane in the total liquid products recovered.
[e] The selectivity to methane was based on the amount of methane analysed in the autoclave headspace at the end of the reaction.

As can be seen from Table 5, using a rhodium catalyst is modified with the tridentate ligand, Xantphos, a substantial increase in selectivity to the carbonylation products, acetic acid and methyl acetate is obtained compared with that obtained in Comparative Examples C and D. In addition, there is a substantial decrease in selectivity to the hydrogenation products, ethanol and its derivatives in Example 2 compared to the selectivity obtained in Comparative Examples C and D.

Similarly, in the absence of a ruthenium promoter, the selectivity to carbonylation products obtained in Example 3 is significantly higher than that obtained in Comparative Example E. Furthermore, there is a substantial decrease in the selectivity to hydrogenation products in Example 3 compared to Comparative Example E.

The invention claimed is:

1. A process for the production of a carboxylic acid and/or the alcohol ester of a carboxylic acid, which process comprises carbonylating an alcohol and/or a reactive derivative thereof with carbon monoxide in a liquid reaction composition in a carbonylation reactor, said liquid reaction composition comprising said alcohol and/or reactive derivative thereof, a carbonylation catalyst, an alkyl halide co-catalyst and, optionally, a finite concentration of water, wherein the catalyst comprises cobalt, rhodium or iridium coordinated with a tridentate ligand or mixtures thereof.

2. A process according to claim 1 and wherein there is also maintained in the reactor, hydrogen at a hydrogen:CO ratio of at least 1:100 and/or the carbon monoxide feed to the reactor comprises at least 1 mol % hydrogen.

3. A process according to claim 2 wherein the hydrogen:CO ratio is at least 1:10.

4. A process according to claim 2 or 3 wherein the carbon monoxide feed comprises at least 5 mol % hydrogen.

5. A process according to claim 2 or 3 wherein carbon monoxide and hydrogen are fed separately or as a mixture to the reactor.

6. A process according to claim 2 or 3 wherein the carbon monoxide and hydrogen are obtained from the reforming of hydrocarbons.

7. A process according to claim 1 or 2 wherein the catalyst comprises rhodium or iridium.

8. A process according to claim 1 or 2 wherein the tridentate ligand has co-ordinating groups containing donor atoms selected from the group consisting of P, As, Sb, O, N, S and carbene.

9. A process according to claim 8 wherein at least two co-ordinating groups have donor atoms selected from the group consisting of P, As and Sb.

10. A process according to claim 1 or claim 2 in which the tridentate ligand has the generic structure A
    wherein L1-L3 are co-ordinating groups having donor atoms and R1 and R2 are linking groups.

11. A process according to claim 10 wherein the structure A co-ordinates to the rhodium, cobalt or iridium metal in a bridging conformation such that two of the co-ordinating groups are mutually trans with respect to the metal.

12. A process according to claim 10 wherein L1 and L3 are mutually trans with respect to the rhodium, iridium or cobalt metal.

13. A process according to claim 12 wherein each of the co-ordinating groups, L1 and L3 have donor atoms selected from the group consisting of P, As and Sb.

14. A process according to claim 10 wherein the donor atoms of L1 to L3 are in a meridional co-ordination mode with respect to the rhodium, iridium or cobalt metal.

15. A process according to claim 10 wherein L1 and L3 co-ordinating groups of the tridentate ligand each comprise a phosphorus donor atom and L2 comprises an oxygen donor atom.

16. A process according to claim 15 wherein the tridentate ligand is of formula P1-R1-O-R2-P2, wherein P1 and P2 are phosphine-containing groups of formula R3R4P and R5R6P respectively and wherein each of R3-R6 is independently selected from the group consisting of substituted and unsubstituted alkenyl, alkyl and aryl groups.

17. A process according to claim 16 wherein each of R3 to R6 is independently a substituted or unsubstituted phenyl.

18. A process according to claim 17 wherein the phenyl is substituted by at least one substituent selected from the group consisting of alkyl, aryl and alkyloxy groups.

19. A process according to claim 18 wherein the substituent is selected from the group consisting of methyl, CF$_3$, ethyl, iso-propyl and methoxy.

20. A process according to claim 18 or claim 19 wherein one or more substituents is ortho.

21. A process according to claim 16 wherein at least one of P1 and P2 is a diphenylphosphine group.

22. A process according to claim 15 wherein the tridentate ligand is selected from the group consisting of substituted and unsubstituted xantphos, phosxantphos, benzoxantphos, thixantphos, isopropxantphos, DPEphos, sixantphos, nixantphos, DBFphos, homoxantphos and R-Nixantphos wherein R is an alkyl or an aryl group.

23. A process according to claim 22 wherein the tridentate ligand is substituted by one or more alkyl groups.

24. A process according to claim 1 or claim 2 wherein the carbonylation catalyst is added to the liquid reaction composition as a pre-formed metal-tridentate ligand complex or is generated in-situ in the liquid reaction composition.

25. A process according to claim 1 or claim 2 wherein the mol ratio of the rhodium, iridium or cobalt metal to the tridentate ligand is in the range 1:1 to 1:2.

26. A process according to claim 1 or claim 2 wherein the liquid reaction composition also comprises a promoter.

27. A process according to claim 26 wherein the promoter is selected from the group consisting of ruthenium, osmium, rhenium, cadmium, mercury, zinc, gallium, indium and tungsten.

28. A process according to claim 1 or claim 2 in which the liquid reaction composition comprises an effective amount of a compound selected from the group consisting of an alkali metal iodide, alkaline earth metal iodide, metal complexes capable of generating I—, salts capable of generating I— and mixtures thereof.

29. A process according to claim 1 or claim 2 wherein the alkyl halide co-catalyst is a $C_1$-$C_4$ alkyl halide.

30. A process according to claim 1 or claim 2 wherein the alcohol is a $C_1$-$C_8$ aliphatic alcohol.

31. A process according to claim 1 or claim 2 wherein the reactive derivative is selected from the group consisting of esters, halides, ethers and mixtures thereof.

32. A process according to claim 1 or claim 2 wherein the liquid reaction composition comprises at least 0.1 wt % water.

33. A process according to claim 32 wherein the liquid reaction composition comprises water in the range 0.1 to 30 wt %.

34. A process according to claim 1 or claim 2 wherein the carbonylation product is acetic acid, methyl acetate and mixtures thereof.

35. A process according to claim 1 or claim 2 in which the Co partial pressure is in the range 1 to 70 barg.

36. A process according to claim 1 or claim 2 wherein the process is a continuous process.

37. A process according to claim 7 wherein catalyst comprises rhodium.

38. A process according to claim 29 wherein the alkyl halide co-catalyst is methyl iodide.

39. A process according to claim 30 wherein the alcohol is methanol.

40. A process according to claim 33 wherein the liquid reaction composition comprises water in the range of 1 to 15 wt %.

41. A process according to claim 33 wherein the liquid reaction composition comprises water in the range of 1 to 10 wt %.

* * * * *